(12) United States Patent
Cotrell et al.

(10) Patent No.: US 10,806,687 B2
(45) Date of Patent: *Oct. 20, 2020

(54) PERSONAL CARE COMPOSITION AND METHOD OF PREPARATION THEREOF

(75) Inventors: Philip Cotrell, Salisbury, NC (US); Samad Syed, Paramus, NJ (US)

(73) Assignee: Innospec Limited, Ellesmere Port, Cheshire (GB)

(*) Notice: Subject to any disclaimer, the term of this patent is extended or adjusted under 35 U.S.C. 154(b) by 0 days.

This patent is subject to a terminal disclaimer.

(21) Appl. No.: 13/384,491

(22) PCT Filed: Jul. 14, 2010

(86) PCT No.: PCT/GB2010/051156
§ 371 (c)(1),
(2), (4) Date: Feb. 23, 2012

(87) PCT Pub. No.: WO2011/007174
PCT Pub. Date: Jan. 20, 2011

(65) Prior Publication Data
US 2012/0141389 A1    Jun. 7, 2012

(30) Foreign Application Priority Data
Jul. 17, 2009 (GB) .................. 0912468.6

(51) Int. Cl.
*A61K 8/46* (2006.01)
*A61K 8/44* (2006.01)
*A61Q 19/10* (2006.01)
*A61Q 11/00* (2006.01)
*A61Q 5/02* (2006.01)

(52) U.S. Cl.
CPC .............. *A61K 8/466* (2013.01); *A61K 8/442* (2013.01); *A61Q 5/02* (2013.01); *A61Q 11/00* (2013.01); *A61Q 19/10* (2013.01); *A61K 2800/596* (2013.01)

(58) Field of Classification Search
None
See application file for complete search history.

(56) References Cited

U.S. PATENT DOCUMENTS

| | | | |
|---|---|---|---|
| 8,673,833 B2* | 3/2014 | Cotrell | 510/125 |
| 8,685,906 B2* | 4/2014 | Cotrell | 510/126 |
| 2008/0255014 A1 | 10/2008 | Luu et al. | |

FOREIGN PATENT DOCUMENTS

| | | |
|---|---|---|
| WO | 1994/009763 A1 | 5/1994 |
| WO | 2005075623 A1 | 8/2005 |
| WO | 2007/130390 A2 | 11/2007 |
| WO | 2009/063250 A2 | 5/2009 |

OTHER PUBLICATIONS

International Search Report and Written Opinion dated Nov. 28, 2011 for International Application No. PCT/GB10/51156.
Amended Safety Assessment of Isethionate Salts as Used in Cosmetics. Cosmetic Ingredient Review Tentative Report for Public Comment dated Jun. 21, 2013, available at www.cir-safety.org.

* cited by examiner

*Primary Examiner* — Dennis J Parad
(74) *Attorney, Agent, or Firm* — Burns & Levinson LLP; Janine M. Susan

(57) ABSTRACT

A stable flowable aqueous composition comprising at least two component surfactants, each component surfactant having a maximum solubility in water at which a saturated solution forms, wherein the total concentration of all surfactants present in the composition is greater than would be obtained by combining equivalent amounts of saturated solutions of the component surfactants; wherein at least one component surfactant includes a compound of formula (I): wherein $R^1$ represents a $C_{4-36}$ alkyl group; each of $R^2$, $R^3$, $R^4$ and $R^5$ independently represents a hydrogen atom or a $C_{1-4}$ alkyl group and wherein at least one of $R^2$, $R^3$, $R^4$ and $R^5$ is not hydrogen and $M^-$ represents a cation.

8 Claims, No Drawings

PERSONAL CARE COMPOSITION AND METHOD OF PREPARATION THEREOF

CROSS-REFERENCE TO RELATED APPLICATIONS

This application is a U.S. national stage application under 35 U.S.C. 371 of co-pending International Application No. PCT/GB10/51156 filed Jul. 14, 2010 and entitled "COMPOSITION AND METHOD", which in turn claims priority to Great Britain Patent Application No. 0912468.6 filed Jul. 17, 2009, both of which are incorporated by reference herein in their entirety for all purposes.

The present invention relates to novel surfactant compositions and to methods and uses relating thereto.

Modern personal care compositions, for example shampoos, conditioners, cleansers, body washes, shower gels, moisturisers and the like are aqueous compositions comprising blends of surfactants and conditioning agents. Personal care formulations are usually prepared by mixing individual surfactants and conditioning agents. The components may be supplied as concentrated solutions which are diluted and/or and combined in appropriate ratios by the formulator. Favoured concentrated components are those which are easy to handle and readily flow and thus can be pumped easily. However to enable a readily flowable composition to be provided the concentration of a particular ingredient is sometimes limited to prevent the formation of a viscous gel or a waxy solid. As a result surfactant concentrates comprising relatively high levels of water are often used as component ingredients in personal care compositions. Such concentrated compositions then need to be transported to various locations worldwide for use in formulation plants. This results in significant volumes of water being transported long distances which is disadvantageous from a cost and environmental perspective.

It would thus be advantageous if more concentrated flowable surfactant compositions could be provided. It would also be beneficial if concentrates including a mixture of surfactants could be supplied as this would reduce the need to transport a plurality of individual components.

According to a first aspect of the present invention there is provided a stable flowable aqueous composition comprising at least two component surfactants, each component surfactant having a maximum solubility in water at which a saturated solution forms, wherein the total concentration of all surfactants present in the composition is greater than would be obtained by combining equivalent amounts of saturated solutions of the component surfactants; wherein at least one component surfactant includes a compound of formula (I):

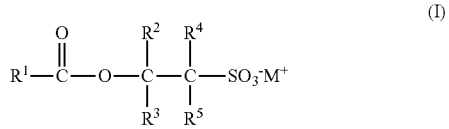

(I)

wherein $R^1$ represents a $C_{4\text{-}36}$ substituted or unsubstituted hydrocarbyl group;

each of $R^2$, $R^3$, $R^4$ and $R^5$ independently represents a hydrogen atom or a $C_{1\text{-}4}$ alkyl group and wherein at least one of $R^2$, $R^3$, $R^4$ and $R^5$ is not hydrogen and $M^+$ represents a cation.

For the avoidance of doubt when referring to an equivalent amount of saturated solution of component surfactant we mean that, as an example, if a composition of the present invention comprises 10 g of surfactant A and 10 g of surfactant B then combining a saturated solution containing 10 g of surfactant A and a saturated solution comprising 10 g of surfactant B would result in a composition having a lower concentration than the composition of the present invention. The skilled person will appreciate that this means that compositions of the present invention have a lower volume for a given mass of surfactant mixture compared with that which would be obtained by mixing saturated solutions.

Thus if a composition of the present invention has a volume V and comprises a plurality n of surfactants wherein a first surfactant is present in an amount having a mass $m_1$, and has a maximum solubility in water $S_1$, a second surfactant is present in an amount having a mass $m_2$ and has a maximum solubility in water $S_2$; and an nth surfactant (when present) is present in an amount having a mass $m_n$ and has a maximum solubility in water $S_n$, then $$V < \frac{m_1}{S_1} + \frac{m_2}{S_2} + \ldots \frac{m_n}{S_n}$$

The maximum solubility in water values refer to the saturation solubility of that component surfactant when no other surfactant or other ingredient is present. Some impurities may be present as commercially available surfactants often contain impurities but the values of $S_1$, $S_2$ and $S_3$ refer to the maximum solubility of the active surfactant present.

Preferably n is less than 10, preferably less than 6. Suitably n may be 2, 3, 4 or 5. In a preferred embodiment n is 2.

The composition of the present invention comprises a greater total concentration of surfactant C than would be obtained by combining saturated solutions of the component surfactants.

The total concentration $$C = \frac{m_1 + m_2 + \ldots m_n}{V}$$

and thus $$C > \frac{m_1 + m_2 + \ldots m_n}{\left(\frac{m_1}{S_1} + \frac{m_2}{S_2} + \ldots \frac{m_n}{S_n}\right)}$$

The composition of the present invention is stable. By this we mean that the composition is suitably provided in a chemically and physically stable form. Thus the composition suitably does not decompose on storage and is chemically stable under the conditions of light, heat and pressure at which it is prepared, used and stored.

The composition is suitably provided in a physically stable form. For example it does not change phase or separate into different phases on standing and is physically stable under the conditions of light, heat and pressure at which it is prepared, stored and used. For example a precipitate does not form from the composition and emulsions do not split.

The composition of the present invention is a flowable composition. By flowable it is meant that the composition can be pumped or made to flow. The composition of the present invention may be any type of composition which can flow including free flowing compositions which can be easily poured and thixotropic compositions which only flow when a stress is applied.

The composition of the present invention may be provided in any suitable form. Preferably it is of substantially uniform consistency. The composition may be in the form of an emulsion. However in preferred embodiments the composition is substantially homogeneous and is present as a single phase composition.

The composition of the present invention may be provided as a gel or paste. Preferably however it is provided as a liquid. It may be provided as viscous liquid which may or may not be thixotropic. It may be provided as a free-flowing liquid.

Preferably the composition of the present invention has a viscosity of less than 120000 cps, preferably less than 110000 cps (mPa·s), more preferably less than 100000 cps (mPa·s), for example less than 95000 cps (mPa·s), suitably less than 90000 cps (mPa·s), preferably less than 85000 cps (mPa·s), for example less than 80000 cps (mPa·s).

When the composition of the present invention is provided as a paste or gel the viscosity is measured at a suitable shear rate, for example 10 to 1000 s$^{-1}$. Viscosities are suitably measured at ambient temperature and pressure.

At least one component surfactant of the present invention includes a compound of formula (I):

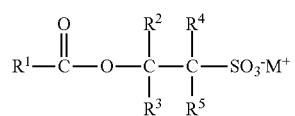

(I)

Preferably $R^1$ is selected from a substituted or unsubstituted alkyl, alkenyl, aryl or alkylaryl group. More preferably $R^1$ is selected from a substituted or unsubstituted alkyl group. Most preferably $R^1$ is an unsubstituted alkyl group.

Preferably $R^1$ represents a $C_{5-30}$ alkyl group, preferably a $C_{7-24}$ alkyl group, more preferably a $C_{7-21}$ alkyl group, most preferably a $C_{7-17}$ alkyl group, for example a $C_{7-15}$ alkyl group.

Preferably $R^2$ represents a $C_{1-4}$ alkyl group, suitably a $C_{1-4}$ alkyl group in which a propyl or butyl group, when present, is straight-chained. Preferably $R^2$ represents an n-propyl, ethyl or, most preferably, a methyl group.

Preferably $R^3$ represents a hydrogen atom.

Preferably one of $R^4$ and $R^5$ represents a hydrogen atom and the other represents a hydrogen atom or a $C_{1-4}$ alkyl group. Preferably one of $R^4$ and $R^5$ represents a hydrogen atom or a $C_{1-4}$ alkyl group in which a propyl or butyl group is straight-chain. Preferably one of $R^4$ and $R^5$ represents an n-propyl, ethyl or methyl group or, most preferably, a hydrogen atom. Most preferably both $R^4$ and $R^5$ represent hydrogen atoms.

In some embodiments the present invention may include a mixture of more than one compound of formula (I). For example an isomeric mixture of compounds of formula (I) may be present. Such a mixture may include, for example a compound in which $R^2$ is alkyl (suitably methyl) and $R^3$, $R^4$ and $R^5$ are all hydrogen and a compound in which $R^5$ is is alkyl (suitably methyl) and $R^2$, $R^3$ and $R^4$ are all hydrogen.

Preferably M$^+$ represents an optionally substituted ammonium cation or, most preferably, a metal cation. Suitable ammonium cations include NH$_4^+$ and the ammonium cation of triethanolamine. Suitable metal cations include alkali metal cations, for example sodium, lithium and potassium cations, and alkaline earth metal cations, for example calcium and magnesium cations. Preferably M$^+$ represents a potassium cation, or, especially, a sodium cation.

$R^1$ may be an alkyl group or an alkenyl group. Preferably $R^1$ is an alkyl group. In some embodiments the component surfactant of the present invention may comprise a mixture of fatty acids to form a mixture of compounds of formula (I) in which $R^1$ may be different.

$R^1$ is the residue of a fatty acid. Fatty acids obtained from natural oils often include mixtures of fatty acids. For example the fatty acid obtained from coconut oil contains a mixture of fatty acids including $C_{12}$ lauric acid, $C_{14}$ myristic acid, $C_{16}$ palmitic acid and $C_8$ caprylic acid.

$R^1$ may include the residue of one or more naturally occuring fatty acids and/or of one or more synthetic fatty acids. In some preferred embodiments $R^1$ consists essentially of the residue of a single fatty acid.

Examples of carboxylic acids from which $R^1$ may be derived residue of include coco acid, butyric acid, hexanoic acid, caproic acid, caprylic acid, capric acid, lauric acid, myristic acid, palmitic acid, palmitoleic acid, stearic acid, oleic acid, linoleic acid, arachidic acid, gadoleic acid, arachidonic acid, eicosapentanoic acid, behinic acid, eruic acid, docosahexanoic lignoceric acid, naturally occurring fatty acids such as those obtained from coconut oil, tallow, palm kernel oil, butterfat, palm oil, olive oil, corn oil, linseed oil, peanut oil, fish oil and rapeseed oil; synthetic fatty acids made as chains of a single length or a selected distribution of chain lengths; and mixtures thereof. Most preferably $R^1$ comprises the residue of lauric acid, that is a saturated fatty acid having 12 carbon atoms or the residue of mixed fatty acids derived from coconut oil.

The compound of formula (I) may be prepared by any of the methods disclosed in the prior art, for example see the methods described in WO94/09763 and WO2005/075623.

In especially preferred embodiments, $R^3$, $R^4$ and $R^5$ are all hydrogen and $R^2$ is ethyl or, most preferably methyl.

In such preferred embodiments the composition of the present invention preferably comprises the reaction product of sodium methyl isethionate and a fatty acid, that is a compound of formula (II):

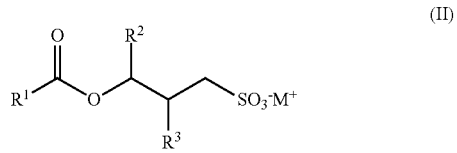

(II)

in which one of $R^2$ and $R^3$ is methyl and the other is hydrogen. Mixtures of these isomers may be present.

Most preferably the composition of the present invention comprises sodium lauryl methyl isethionate and/or sodium cocoyl methyl isethionate.

In addition to the component surfactant including compounds of formula (I) the composition of the present invention includes one or more further component surfactants. Compounds of formula (I) are known to be mild to the skin and are thus particularly suitable for use in personal care formulations. The one or more further component surfactants included in the composition of the present invention are also suitably mild to the skin.

Preferred surfactants for use herein are those which are commonly used in personal care formulations. Different surfactants are approved for different purposes and the skilled person will understand the type of surfactant that could be used for a given application. Of course it will also be appreciated that the list of cosmetically approved surfactants is continually changing and thus the composition of the present invention is not limited to such surfactants.

The one or more further component surfactants for use in the present invention may be selected from anionic surfactants, cationic surfactants, amphoteric surfactants, non-ionic surfactants and mixtures thereof. Preferably the one or more further component surfactants are selected from anionic surfactants, amphoteric surfactants and mixtures thereof.

Suitable anionic surfactants for use in the composition of the present invention include salts of $C_{12}$ to $C_{18}$ carboxylic acids, ethoxylated carboxylic acids, ester carboxylates and ethoxylated ester carboxylates and sarcosinates. Other suitable anionic surfactants include sulfates and sulfonates, for example alkyl sulfates, alkyl ether sulfates, alcohol sulfates, alcohol ether sulfates, α-olefin sulfonates, linear alkyl sulfonates; and phosphate esters.

Suitable anionic surfactants may be selected from salts of fatty acids; alkali metal salts of mono- or dialkyl sulfates; mono- or dialkyl ether sulfates; lauryl ether sulfates; alkyl sulfonates; alkyl aryl sulfonates; primary alkane disulfonates; alkene sulfonates; hydroxyalkane sulfonates; alkyl glyceryl ether sulfonates; alpha-olefinsulfonates; alkyl phosphates; sulfonates of alkylphenolpolyglycol ethers; salts of alkyl sulfopolycarboxylic acid esters; alkyl sulfosuccinates and salts thereof, alkyl ether sulfosuccinates and salts thereof, non-acylated alkyl isethionates; fatty acid taurates; acyl taurates; products of condensation of fatty acids with oxy- and aminoalkanesulfonic acids; sulfated derivatives of fatty acids and polyglycols; alkyl and acyl sarcosinates; sulfoacetates; alkyl phosphates; alkyl phosphate esters; acyl lactates; alkanolamides of sulfated fatty acids and salts of lipoamino acids. Particularly exemplary salts of the above, where applicable, are the sodium, potassium, ammonium, magnesium and triethanolamine salts.

Particularly preferred anionic surfactants for use herein include sodium methyl cocoyl taurate, sodium lauryl sarcosinate, alcohol sulfates and alcohol ether sulfates.

Suitable non-ionic surfactants for use herein include alcohol ethoxylates and ethylene oxide/propylene oxide copolymer derived surfactants, sugar esters, especially sorbitan esters, alkyl polyglucosides, fatty acid ethoxylates or polyethylene glycol esters and partial esters, alkanolamides and amineoxides.

Especially preferred non-ionic surfactants for use herein include fatty acid alkanolamides, ethylene glycol stearate and ethylene glycol distearate.

Suitable non-ionic surface-active agents may be selected from the following: reaction products of compounds having a hydrophobic group and a reactive hydrogen atom, for example aliphatic alcohols, acids, amides or alkyl phenols with alkylene oxides, especially ethylene oxide either alone or with propylene oxide (for example alkyl ($C_6$-$C_{22}$) phenol-ethylene oxide condensates, the condensation products of aliphatic ($C_8$-$C_{18}$) primary or secondary linear or branched alcohols with ethylene oxide, and products made by condensation of ethylene oxide with the reaction products of propylene oxide and ethylenediamine); long chain tertiary amine oxides, long chain tertiary phosphine oxides and dialkyl sulphoxides; alkyl amine oxides, alkyl amido amine oxides; alkyl tertiary phosphine oxides; alkoxyl alkyl amines; sorbitan; sorbitan esters; sorbitan ester alkoxylates; glycerol ester alkoxylates; sucrose esters; sugar amides, such as a polysaccharide amide; lactobionamides; and alkyl polysaccharide nonionic surfactants, for example alkylpolyglycosides. Preferred non-ionic surfactants are sucroglycerides and ethyoxylated fatty alcohols, especially those derived from lauryl, cetylstearyl, stearyl, cetyl and oleocetyl alcohols.

Suitable cationic surfactants for use herein are typically based on fatty amine derivates or phosphonium quaternary ions, and quaternary ammonium compounds.

Suitable cationic surfactants for use herein include tertiary amine salts, mono alkyl trimethyl ammonium chloride, mono alkyl trimethyl ammonium methyl sulphate, dialkyl dimethyl ammonium chloride, dialkyl dimethyl ammonium methyl sulphate, trialkyl methyl ammonium chloride and trialkyl methyl ammonium methyl sulfate.

Suitable amphoteric surfactants include those based on fatty nitrogen derivates and those based on betaines.

Suitable amphoteric or zwitterionic surfactants may be selected from betaines, for example alkyl betaines, alkylamidopropyl betaines, alkylamidopropyl hydroxy sultaines, alkylampho acetates, alkylamphodiacetates, alkylamphopropionates, alkylamphodipropionates, alkyliminodipropionates and alkyliminodiacetate.

Amphoteric or zwitterionic surfactants for use in the compositions of the present invention may include those which have an alkyl or alkenyl group of 7 to 22 carbon atoms and comply with an overall structural formula:

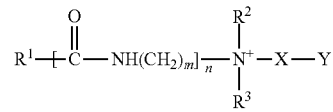

where $R^1$ is alkyl or alkenyl of 7 to 22 carbon atoms; $R^2$ and $R^3$ are each independently alkyl, hydroxyalkyl or carboxyalkyl of 1 to 6 carbon atoms; m is 2 to 4; n is 0 or 1; X is alkylene of 1 to 6 carbon atoms optionally substituted with hydroxyl; and Y is $-CO_2$ or $-SO_3$.

Amphoteric or zwitterionic surfactants may include simple betaines of formula:

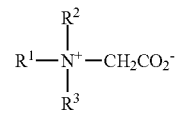

and amido betaines of formula:

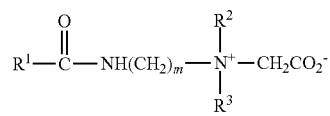

where m is 2 or 3.

In both formulae $R^1$, $R^2$ and $R^3$ are as defined previously. $R^1$ may, in particular, be a mixture of $C_{12}$ and $C_{14}$ alkyl groups derived from coconut so that at least half, preferably at least three quarters, of the groups $R^1$ has 10 to 14 carbon atoms. $R^2$ and $R^3$ are preferably methyl.

Amphoteric or zwitterionic surfactants may include sulphobetaines of formula:

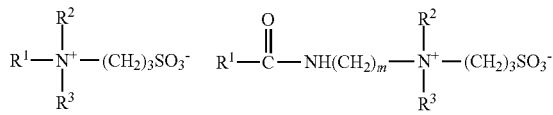

where m is 2 or 3, or variants of these in which —$(CH_2)_3SO_3^-$ is replaced by

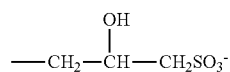

where $R^1$, $R^2$ and $R^3$ in these formulae are as defined previously.

Amphoteric or zwitterionic surfactants may include amphoacetates and diamphoacetates. Amphoacetates generally conform to the following formula:

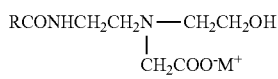

Diamphoacetates generally conform to the following formula:

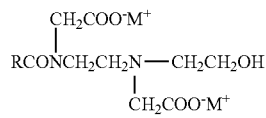

where R is an aliphatic group of 8 to 22 carbon atoms and M is a cation such as sodium, potassium, ammonium, or substituted ammonium.

Suitable acetate-based surfactants include lauroamphoacetate; alkyl amphoacetate; cocoampho(di)acetate; cocoamphoacetate; disodium cocoamphodiacetate; sodium cocoamphoacetate; disodium cocoamphodiacetate; disodium capryloamphodiacete; disodium lauroamphoacetate; sodium lauroamphoacetate and disodium wheatgermamphodiacetate.

Suitable betaine surfactants include alkylamido betaine; alkyl betaine, $C_{12/14}$ alkyldimethyl betaine; cocoamidopropylbetaine; tallow bis(hydroxyethyl) betaine; hexadecyldimethylbetaine; cocodimethylbetaine; alkyl amido propyl sulfo betaine; alkyl dimethyl amine betaine; coco amido propyl dimethyl betaine; alkyl amido propyl dimethyl amine betaine; cocamidopropyl betaine; lauryl betaine; laurylamidopropl betaine, coco amido betaine, lauryl amido betaine, alkyl amino betaine; alkyl amido betaine; coco betaine; lauryl betaine; diemethicone propyl PG-betaine; oleyl betaine; N-alkyldimethyl betaine; coco biguamide derivative, $C_8$ amido betaine; $C_{12}$ amido betaine; lauryl dimethyl betaine; alkylamide propyl betaine; amido betaine; alkyl betaine; cetyl betaine; oleamidopropyl betaine; isostearamidopropyl betaine; lauramidopropyl betaine; 2-alkyl-N-carboxymethyl-N-hydroxyethyl imidazolinium betaine; 2-alkyl-N-carboxyethyl-N-hydroxyethyl imidazolinium betaine; 2-alkyl-N-sodium carboxymethyl-N-carboxymethyl oxyethyl imidazolinium betaine; N-alkyl acid amidopropyl-N,N-dimethyl-N-(3-sulfopropyl)-ammonium-betaine; N-alkyl-N,N-dimethyl-N-(3-sulfopropyl)-ammonium-betaine; cocodimethyl betaine; apricotamidopropyl betaine; isostearamidopropyl betaine; myristamidopropyl betaine; palmitamidopropyl betaine; cocamidopropyl hydroxyl sultaine; undecylenamidopropyl betaine; cocoamidosulfobetaine; alkyl amido betaine; $C_{12/18}$ alkyl amido propyl dimethyl amine betaine; lauryldimethyl betaine; ricinol amidobetaine; tallow aminobetaine.

Suitable glycinate surfactants include cocoamphocarboxyglycinate; tallowamphocarboxygycinate; capryloamphocarboxyglycinate, oleoamphocarboxyglycinate, bis-2-hydroxyethyl tallow glycinate; lauryl amphoglycinate; tallow polyamphoglycinate; coco amphoglycinate; oleic polyamphoglycinate; N—$C_{10/12}$ fatty acid amidoethyl-N-(2-hydroxyethyl)-glycinate; N—$C_{12/18}$-fatty acid amidoethyl-N-(2-hydroxyethyl)-glycinate; dihydroxyethyl tallow gycinate.

The selection of further component surfactants for use herein will depend on the intended end use of the composition of the present invention. The composition may for example be used in shampoos, hair conditioners, skin cleansing compositions, shower gels, bath products, hand cleansers, oral care products, emulsions for skin care use or other personal care applications.

Sodium lauryl sulfate has long been used in shampoos as it provides a creamy feel on application and a tight foam. Clear shampoos often include sodium laurylethersulfate (2EO). Other surfactants included in shampoos include alkanoamides for example cocodiaethanolamide; triethanol amine lauryl sulfate; sodium laureth-2 sulfate; imidazoline derived surfactants; lauric sorbitan ester 20EO; quaternary hydrolysed proteins, diamethicone copolyol; lanolin derivates; and cationic guar gum derivates. Commonly used surfactants for shampoos include sodium laurylsulfate and other alkyl sulfates and ether sulfates as well as sulfocsuccinates, amine oxides, sodium laurethcarboxylates, sodium lauroylsarcosinates and amphoteric cocoamidopropyl betaine, sodium amphocarboxyglycinate and alkylpolyamino carboxylates.

Hair conditioners often contain cationic surfactants especially quaternary ammonium compounds as they counter static caused by shampoos. Suitable hair conditioners may include cetyl trimeythl ammonium bromide and behenyl trimethyl ammonium chloride.

Skin cleansing soaps often include sodium cocoyl isethionates, acyl N-methyl taurates, a-olefin sulfonates, fatty alcohol sulfates, sulfo-succinate monoesters, alkylsulfoacetate, gylcerylestersulfate and acylglutamate.

Shower gels often include similar surfactants to those used in shampoos with sodium lauryl sulfate being particularly commonly used.

Foam baths often include sodium laureth-3 sulphate (3EO) to provide bubbles and also often include cocoyl methyl taurate and alkanolamides or polyethoxylated lanolin.

Hand cleaners may include a-olefin sulfonates, sodium laurylsulfate, ammonium laurylsulfate or cocoamidopropyl betaine.

Toothpates often include sodium lauryl sulfate, sodium lauroyl sarcosinates or alkylpolyglycosides.

Mouth washes may include sodium laurylsulfate, sodium methyl cocoyl taurate; coco amidopropyl betaine and biocidal cationic surfactants for example cetyl pyridiniumchloride.

Emulsion type skin type products may include a variety of component surfactants including glyceryl monstearate; and derivates thereof; cetostearyl alcohol; ethoxylate and sodium cetylsulfate.

The composition of the present invention comprises a compound of formula (I) in combination with one or more further component surfactants. Preferably the weight ratio of the compound of formula (I) to the one or more further component surfactants is at least 0.05 to 1, preferably at least 0.1 to 1, suitably at least 0.2 to 1 for example at least 0.3 to 1 or 0.4 to 1. The weight ratio of the components of formula (I) to the total weight of the remaining component surfactants may be up to 50 to 1, for example up to 25 to 1, suitably up to 15 to 1, for example up to 10 to 1, up to 8 to 1 or up 5 to 1.

Suitably the compound of formula (I) is present in the composition of the present invention in an amount of at least 0.1 wt %, preferably at least 1 wt %, suitably at least 2.5 wt %, preferably at least 5 wt %, for example at least 7.5 wt %, at least 10 wt %, at least 12.5 wt % or at least 15 wt %.

Suitably the compound of formula (I) is present in the composition of the present invention in an amount of up to 70 wt %, preferably up to 60 wt %, suitably up to 50 wt %.

The total amount of further component surfactants other than those compounds of formula (I) present in the composition of the present invention is preferably at least 0.1 wt % suitably at least 1 wt %, for example at least 2.5 wt %, preferably at least 5 wt %, for example at least 7.5 wt %, at least 10 wt % or at least 12.5 wt % or at least 15 wt %. The total amount of further component surfactants other than those compounds of formula (I) present in the composition of the present invention is preferably up to 70 wt %, preferably up to 60 wt %, suitably up to 50 wt %.

In some embodiments the composition of the present invention comprises two major component surfactants. In some embodiments the composition of the present invention includes two major component surfactants. By major component surfactants we mean these account for at least 90 wt %, preferably at least 95 wt % of all component surfactants present in the composition.

For the avoidance of doubt the definitions of the above amounts of surfactant refer to the actual amount of active surfactant compound present in the composition. However the skilled person will appreciate that commercially available surfactant compositions are usually supplied as impure compounds. The levels of impurity present in commercial surfactants is typically from 10 to 25% by weight and these impurities usually contain unreacted starting materials and/or byproducts.

Thus a composition comprising approximately 40 wt % of active surfactant may in fact comprise a total mass of about 50 wt % of non-volatile surfactant-based material. The compositions of the present invention preferably comprise from 30 to 50 wt %, preferably 35 to 48 wt %, for example 38 to 45 wt % of component surfactants in total (on mass of active only).

The compositons preferably comprise from 30 to 70 wt %, preferably 35 to 65 wt %, more preferably from 40 to 60, for example from 45 to 55 wt % of total non-volatile surfactant-based material. The term "non-volatile surfactant-based material" includes the active component surfactant used in the present invention and any other residue which may be present as an impurity in a commercially available surfactant mixture. Non-volatile impurities which cannot be easily separated may also be present in synthetically prepared component surfactant compositions.

In especially preferred embodiments the present invention provides a composition comprising sodium lauryl methyl isethionate and one or more further component surfactants selected from cocoamidopropyl betaine, sodium methylcocoyltaurate, sodium lauroamphoacetate and sodium lauroylsarcosinate.

The present invention provides an aqueous composition. In some embodiments the composition may comprise one or more further solvents in addition to water. Such suitable co-solvents may include polar compounds for example alcohols, glycols and the like.

However in preferred embodiments water is the major solvent present in the composition of the present invention and suitably comprises at least 90 wt % of all solvents present, preferably at least 95 wt %, more preferably at 99 wt %. In especially preferred embodiments water is substantially the only solvent present. However the compositions of the present invention are concentrated compositions in which a much lower concentration of water is present than has been previously achieved using mixtures of surfactants of this kind.

Preferably the composition of the present invention comprises less than 80 wt % water, preferably less than 75 wt %, more preferably less than 70 wt %, suitably less than 65 wt %, more preferably less than 60 wt %, preferably less than 58 wt %, most preferably less than 55 wt %. In some preferred embodiments the composition of the present invention may comprise less than 52 wt % water.

Preferably the composition consists essentially of the two or more component surfactants, water and any non-volatile impurities present in the source of the surfactant. Any further ingredients are preferably present in an amount of less than 10 wt %, preferably less than 5 wt %.

The composition of the present invention may further comprise a pH control agent. Any suitable acid or base may be used as a pH modifier. Preferred pH modifiers are those which are cosmetically acceptable and the selection of an appropriate acid or base would be within the competence of the person skilled in the art. An especially preferred acid is critic acid. An especially preferred base is sodium hydroxide.

Suitably the composition of the present invention has a pH of at least 4, preferably at least 4.5, suitably at least 5, for example at least 5.5 or at least 5.8. Preferably the composition of the present invention has a pH of less than 10, preferably less than 9, for example less than 8.5 or less than 8.3.

In some embodiments the composition of the present invention further comprises a chelating agent. Suitable chelating agents include amino carboxylic acid and amino phosphoric acid chelating agents. Especially preferred chelating agents are ethylene diamine tetraacetric acid and ethylene diamine disuccinic acid. A chelating agent is usually present in an amount of less than 5 wt %, for example less than 2.5 wt %.

The composition of the present invention may be prepared by any suitable means. It may typically be prepared by adding a solid source of a first component surfactant to a commercially available saturated solution of a second component surfactant. Further water may be added as necessary and the mixture may be gently heated. Alternatively a first component surfactant may be added as a molten liquid to an aqueous solution of one or more component surfactants.

The present invention provides a concentrated multiple surfactant containing composition. This may be used for any suitable purpose. Preferably the composition is used in the preparation of personal care compositions. Thus the present invention further provides the use of a composition of the first aspect in the preparation of a personal care composition. Suitably the personal care composition may be selected from a hair care composition, a skin care composition or an oral care composition.

The invention thus further provides a method of preparing a personal care composition, the method comprising diluting a composition of the first aspect to provide a desired final concentration of component surfactants. The method will typically involve blending the diluted composition with further components and is within the competence of the person skilled in the art.

The invention will now be further defined with reference to the following non limiting examples.

In these examples the following commerically available surfactants were used:

Surfactant A—Sodium Lauryl Methyl Isethionate

This surfactant was used as a 100% non-volatile solid material comprising 85 wt % of the active surfactant compound.

Surfactant B—Cocamidopropyl Betaine

This surfactant was supplied as an aqueous solution containing 35 wt % non-volatile compounds and 30 wt % of the active surfactant compound.

Surfactant C—Sodium Methyl Cocoyl Taurate

This surfactant was supplied as a cloudy viscous paste containing 38 wt % non-volatile compounds and 30 wt % of the active surfactant compound.

Surfactant D—Sodium Lauro Ampho Acetate

This surfactant was supplied as an aqueous solution containing 38 wt % non-volatile compounds and 31 wt % of the active surfactant compound.

Surfactant E—Sodium Lauroyl Sarcosinate

This surfactant was supplied as an aqueous solution containing 30 wt % non-volatile compounds and 28 wt % of the active surfactant compound.

Prior to use in examples 1 to 5 surfactants A, B, C, D and E were concentrated in vacuo to provide a composition comprising 50 wt % of non-volatile surfactant-based material.

EXAMPLE 1

The compositions detailed in table 1 were prepared by adding the specified amount of surfactant A to solution of surfactant B comprising 50 wt % non-volatile material. The mixture was heated and further water was added if required.

TABLE 1

| Surfactant A (wt % non-volatile) | Surfactant B (wt % non-volatile) | wt % total non-volatile surfactant material | wt % active surfactant | Appearance | Viscosity (cps) | pH |
| --- | --- | --- | --- | --- | --- | --- |
|  | 50 | 50 | 42.86 | Solid | — | 7.5 |
| 10 | 40 | 50 | 42.79 | Paste | 166600 | 7 |
| 15 | 35 | 50 | 42.75 | Paste | 104000 | 7.1 |
| 20 | 30 | 50 | 42.71 | Thick liquid | 65000 | 7.2 |
| 25 | 25 | 50 | 42.68 | Flowable liquid | 11000 | 7 |
| 30 | 20 | 50 | 42.64 | Flowable liquid | 6230 | 7.1 |
| 35 | 15 | 50 | 42.61 | Flowable liquid | 5430 | 7 |

EXAMPLE 2

The compositions detailed in table 2 were prepared by adding the specified amount of surfactant A to a solution of surfactant C comprising 50 wt % non-volatile material. The mixture was heated and further water was added if required.

TABLE 2

| Surfactant A (wt % non-volatile) | Surfactant C (wt % non-volatile) | wt % total non-volatile surfactant material | wt % total active surfactant | Appearance | Viscosity (cps) | pH |
| --- | --- | --- | --- | --- | --- | --- |
|  | 50 | 50 | 39.47 | Solid | — | 7.5 |
| 10 | 40 | 50 | 40.08 | Semi solid | — | 7.3 |
| 15 | 35 | 50 | 40.38 | Flowable liquid | 64787 | 7.3 |
| 20 | 30 | 50 | 40.68 | Flowable liquid | 44537 | 7.26 |
| 25 | 25 | 50 | 40.99 | Flowable liquid | 30700 | 7.3 |
| 30 | 20 | 50 | 41.29 | Clear liquid | 20327 | 7.3 |
| 35 | 15 | 50 | 41.59 | Clear liquid | 11378 | 7.4 |

EXAMPLE 3

The compositions detailed in table 3 were prepared by adding the specified amount of surfactant A to a solution of surfactant D comprising 50 wt % non-volatile material. The mixture was heated and further water was added if required.

TABLE 3

| Surfactant A (wt % non-volatile) | Surfactant D (wt % non-volatile) | wt % total non-volatile surfactant material | wt % active surfactant | Appearance | Viscosity (cps) | pH |
|---|---|---|---|---|---|---|
|  | 50 | 50 | 40.79 | Thick solid | 88000 | 7.5 |
| 10 | 40 | 50 | 41.13 | Thick solid | 21400 | 7.2 |
| 15 | 35 | 50 | 41.30 | Flowable liquid | 13730 | 7.1 |
| 20 | 30 | 50 | 41.47 | Flowable liquid | 7030 | 7 |
| 25 | 25 | 50 | 41.64 | Flowable liquid | 6070 | 7 |
| 30 | 20 | 50 | 41.82 | Flowable liquid | 5650 | 7.1 |
| 35 | 15 | 50 | 41.99 | Flowable liquid | 5260 | 7.2 |

EXAMPLE 4

The compositions detailed in table 4 were prepared by adding the specified amount of surfactant A to a solution of surfactant E comprising 50 wt % non-volatile material. The mixture was heated and further water was added if required.

TABLE 4

| Surfactant A (wt % non-volatile) | Surfactant E (wt % non-volatile) | wt % total non-volatile surfactant material | wt % active surfactant | Appearance | Viscosity (cps) | pH |
|---|---|---|---|---|---|---|
|  | 50 | 50 | 46.67 | solid | — | 7.5 |
| 10 | 40 | 50 | 45.83 | Thick solid | 150500 | 7.2 |
| 15 | 35 | 50 | 45.42 | Thick solid | 96000 | 7.2 |
| 20 | 30 | 50 | 45.00 | Flowable liquid | 74050 | 7.2 |
| 25 | 25 | 50 | 44.58 | Flowable liquid | 25600 | 7.1 |
| 30 | 20 | 50 | 44.17 | Flowable liquid | 12400 | 7.2 |
| 35 | 15 | 50 | 43.75 | Flowable liquid | 6850 | 7.2 |

EXAMPLE 5

Further compositions as detailed in table 5 were prepared by adding the specified amount of surfactant A to mixed aqueous solutions of the specified amounts of surfactants B, C, D and E. The percentages of component surfactants A to E in table 5 refer to the total amount of non-volatile material for each of these components. The mixture was heated and further water was added if required.

TABLE 5

| A wt % | B wt % | C wt % | D wt % | E wt % | total non-volatile wt % | active wt % | appearance | viscosity (cps) | pH |
|---|---|---|---|---|---|---|---|---|---|
| 35 | 7.5 | 7.5 | 0 | 0 | 50 | 42.10 | flowable liquid | 6500 | 7.5 |
| 35 | 7.5 | 0 | 0 | 7.5 | 50 | 43.18 | flowable liquid | 5700 | 8 |
| 35 | 5 | 0 | 5 | 5 | 50 | 42.78 | flowable liquid | 5000 | 8.2 |
| 35 | 10 | 0 | 5 | 0 | 50 | 42.40 | flowable liquid | 8800 | 8.1 |

TABLE 5-continued

| A wt % | B wt % | C wt % | D wt % | E wt % | total non-volatile wt % | active wt % | appearance | viscosity (cps) | pH |
|---|---|---|---|---|---|---|---|---|---|
| 35 | 7.5 | 0 | 7.5 | 0 | 50 | 42.30 | flowable liquid | 7500 | 8.2 |
| 35 | 5 | 5 | 5 | 0 | 50 | 42.06 | flowable liquid | 8500 | 8.2 |
| 35 | 0 | 0 | 7.5 | 7.5 | 50 | 42.87 | flowable liquid | 5700 | 8.2 |
| 15 | 25 | 5 | 5 | 0 | 50 | 42.20 | semi solid | 157000 | 8 |
| 25 | 15 | 5 | 5 | 0 | 50 | 42.13 | flowable liquid | 20000 | 8.2 |
| 15 | 12 | 12 | 11 | 0 | 50 | 41.48 | flowable liquid | 12500 | 8.1 |

EXAMPLE 6

Compositions of the present invention were prepared having the components shown in table 6. As this table also shows the compositions of the present invention provide highly concentrated liquid compositions whereas compositions of the prior art which do not include a compound of formula (I) are solid or semi-solid.

Surfactant F is sodium lauryl isethionate and was supplied as a 100% non-volatile solid material comprising 78 wt % active surfactant.

TABLE 6

| Surfactant F wt % non-volatile | 35 | 35 | 35 | | | | | |
|---|---|---|---|---|---|---|---|---|
| surfactant A wt % non-volatile | | | | 35 | 35 | 35 | 25 | 20 |
| surfactant C wt % non-volatile | 5 | 20 | 40 | 5 | 20 | 40 | 65.79 | 75 |
| EDTA (40%) | 2.6 | 2.6 | 2.6 | 2.6 | 2.6 | 2.6 | 2.625 | 2.625 |
| 50% Citric Acid/dilute NaOH to pH 6-8 | QS | QS | QS | QS | QS | QS | QS | QS |
| D.I. Water | to 100 | to 100 | to 100 | to 100 | to 100 | to 100 | to 100 | to 100 |
| Appearance | Hazy solid | Hazy semi-solid | Hazy semi-solid | clear liquid | clear liquid | clear liquid | clear liquid | Hazy Thick liquid |
| pH | 6.74 | 6.71 | 6.52 | 6.6 | 6.9 | 6.89 | 7.9 | 7.8 |
| Viscosity(CPS) | Not feasible | Not feasible | Not feasible | 5750 | 6600 | 3650 | 23330 | 44500 |
| wt % total non-volatile surfactant material | 37.94 | 43.64 | 51.24 | 37.94 | 43.64 | 51.24 | 51.05 | 49.55 |
| Total active surfactants wt % | 28.8 | 33.3 | 39.3 | 31.3 | 35.8 | 41.8 | 41.0 | 39.5 |

The invention claimed is:

1. A stable flowable aqueous composition comprising less than 65 wt % water and at least two component surfactants, each component surfactant having a maximum solubility in water at which a saturated solution forms, wherein the total concentration of all surfactants present in the composition is greater than would be obtained by combining equivalent amounts of saturated solutions of the component surfactants and wherein the total amount of active component surfactants is 30 to 50 wt %; wherein at least one component surfactant includes a compound of formula (I):

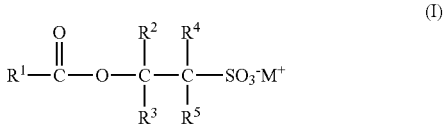

wherein $R^1$ represents a $C_{4\text{-}36}$ alkyl group;

each of $R^2$, $R^3$, $R^4$ and $R^5$ independently represents a hydrogen atom or a $C_{1\text{-}4}$ alkyl group and wherein at least one of $R^2$, $R^3$, $R^4$ and $R^5$ is not hydrogen and $M^+$ represents a cation; and a second component surfactant comprises one or more surfactants selected from the group consisting of alkyl betaines, alkylamidopropyl betaines, alkylamidopropyl hydroxy sultaines, alkylampho acetates, alkylamphodi-acetates, alkylamphopropionates, alkylamphodipropionates, alkyliminodipropionates, alkyliminodiacetate, salts of $C_{12}$ to $C_{18}$ carboxylic acids, ethoxylated carboxylic acids, ester carboxylates and ethoxylated ester carboxylates and sarcosinates; alkyl sulfates, alkyl ether sulfates, alkyl aryl sufonates, alkyl amine oxides, alkylamidoamine oxides, alcohol ethoxlates, ethylene oxide/propylene oxide copolymer derived surfactants, sugar esters, sorbitan ester alkoxylates, glyceryl ester alkoxylates, alkyl polyglucosides, fatty acid ethoxylates, polyethylene glycol esters and partial esters, fatty alkanolamides, quaternary ammonium compounds, tertiary amine salts, salts of fatty acids; alkali metal salts of mono- or dialkyl sulfates; mono- or dialkyl ether sulfates; lauryl ether sulfates; alkyl sulfonates; alkyl aryl sulfonates; primary alkane disulfonates; alkene sulfonates; hydroxyalkane sulfonates; alkyl glyceryl ether sulfonates; alpha-olefinsulfonates; alkyl phosphates; sulfonates of alkylphenolpolyglycol ethers; salts of alkyl sulfopolycarboxylic acid esters; alkyl sulfosuccinates and salts thereof, alkyl ether sulfosuccinates and salts thereof, non-acylated alkyl isethionates; fatty acid taurates; acyl taurates; products of condensation of fatty acids with oxy- and aminoalkanesulfonic acids; sulfated derivatives of fatty acids and polyglycols; alkyl and acyl sarcosinates; sulfoacetates; alkyl phosphates; alkyl phosphate esters; acyl lactates; alkanolamides of sulfated fatty acids; salts of lipoamino acids; and the sodium, potassium, ammonium, magnesium and triethanolamine salts of the above; wherein the total amount of the second component surfactant is at least 10 wt % and the composition comprises 35 to 65 wt % of non-volatile surfactant based material.

2. The composition according to claim 1 wherein $R^2$ is alkyl and each of $R^3$, $R^4$ and $R^5$ is hydrogen.

3. The composition according to claim 1 wherein $R^1$ is a $C_{10}$ to $C_{16}$ alkyl group.

4. The composition according to claim 1 which has a viscosity of less than 100000 cps (mPa·s).

5. The composition according to claim 1 having a volume V which comprises a plurality n of surfactants
wherein a first surfactant is present in an amount having a mass mi, and has a maximum solubility $S_1$,
a second surfactant is present in an amount having a mass $m_2$ and has a maximum solubility $S_2$; and
an nth surfactant (when present) is present in an amount having a mass $m_n$ and has a maximum solubility $S_n$, wherein $$V < \frac{m_1}{S_1} + \frac{m_2}{S_2} + \ldots \frac{m_n}{S_n}.$$

6. The composition according to claim 1 comprising less than 60 wt % water.

7. The composition according to claim 1, wherein the total amount of active component surfactants is 35 to 48 wt %.

8. The composition according to claim 1, wherein the total amount of the second component surfactant is at least 12.5 wt %.

* * * * *

UNITED STATES PATENT AND TRADEMARK OFFICE
CERTIFICATE OF CORRECTION

PATENT NO. : 10,806,687 B2
APPLICATION NO. : 13/384491
DATED : October 20, 2020
INVENTOR(S) : Philip Cotrell et al.

Page 1 of 1

It is certified that error appears in the above-identified patent and that said Letters Patent is hereby corrected as shown below:

In the Claims

In Column 18, Line 8 of Claim 5, in the formula:
"mass mi"
Should read:
-- mass $m_1$ --

Signed and Sealed this
Twelfth Day of January, 2021

Andrei Iancu
*Director of the United States Patent and Trademark Office*